US007007863B2

(12) United States Patent
Kotary et al.

(10) Patent No.: US 7,007,863 B2
(45) Date of Patent: Mar. 7, 2006

(54) WICK-BASED DELIVERY SYSTEM WITH WICK MADE OF DIFFERENT COMPOSITE MATERIALS

(75) Inventors: Kara L. Kotary, Racine, WI (US); Adam Hagop Buchaklian, East Troy, WI (US); Robert J. Kopanic, Racine, WI (US); Padma Prabodh Varanasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 8 days.

(21) Appl. No.: 10/266,512

(22) Filed: Oct. 8, 2002

(65) Prior Publication Data

US 2004/0065749 A1     Apr. 8, 2004

(51) Int. Cl.
*A61L 9/04*      (2006.01)

(52) U.S. Cl. .............................. 239/44; 239/34; 239/47; 239/49; 239/145; 222/187; 159/906; 122/366

(58) Field of Classification Search ............ 239/44–47, 239/145, 34, 49, 51.5, 326; 222/187; 392/395; 159/906; 122/366; 428/304.4, 316.6; 47/81; 261/99, 104

See application file for complete search history.

(56) References Cited

U.S. PATENT DOCUMENTS

| 4,286,754 | A | * | 9/1981 | Jones ............................ 239/6 |
|---|---|---|---|---|
| 4,468,428 | A | * | 8/1984 | Early et al. .................. 428/221 |
| 5,749,519 | A | * | 5/1998 | Miller .......................... 239/44 |
| 6,104,867 | A | * | 8/2000 | Stathakis et al. ............ 392/403 |
| 6,217,315 | B1 | * | 4/2001 | Mifune et al. ............... 431/321 |
| 6,486,231 | B1 | * | 11/2002 | Hekal .......................... 523/102 |
| 6,662,802 | B1 | * | 12/2003 | Smith et al. ........... 128/203.16 |
| 2002/0076214 | A1 | | 6/2002 | Vieira |
| 2002/0146242 | A1 | | 10/2002 | Vieira |
| 2003/0005620 | A1 | * | 1/2003 | Ananth et al. ................. 43/125 |
| 2003/0168520 | A1 | | 9/2003 | Triplett et al. |

FOREIGN PATENT DOCUMENTS

| EP | 0 669 137 A1 | 8/1995 |
|---|---|---|
| EP | 1 247 447 A1 | 10/2002 |
| FR | 2 483 782 | 6/1980 |
| GB | 2 194 442 A | 3/1988 |
| WO | WO 01/05442 A1 | 1/2001 |
| WO | WO 03/075967 A1 | 9/2003 |

* cited by examiner

*Primary Examiner*—Thomas Denion
*Assistant Examiner*—Kyle M. Riddle (57) ABSTRACT

A composite wick for delivering two liquids with different properties to a surface includes a first section provided for delivering a first liquid to the surface of the wick and a second section provided for delivering a second liquid to the surface of the wick. Preferably, the first section is made of hydrophobic materials and the second section is made of hydrophilic materials. Also, a composite wick includes a first section made of either a porous ceramic-based material or a porous sand-based material and a second section made of a porous plastic material, wherein the first and second section preferably are formed as concentric cylinders, with the first section being disposed within the second section.

64 Claims, 5 Drawing Sheets

WICK-BASED DELIVERY SYSTEM WITH WICK MADE OF DIFFERENT COMPOSITE MATERIALS

BACKGROUND OF THE INVENTION

1. Field of the Invention

The present invention relates to a device for transporting liquids, such as insect repellant, fragrances, or insecticides, from a reservoir to a surface exposed to the ambient air.

2. Description of the Related Art

Devices that release vapors into the ambient air are well-known in the art. Generally, the purpose of these devices is to deodorize or disinfect the ambient air, or to distribute toxins into the air to kill or repel unwanted pests, such as mosquitoes.

To achieve the goal of dispensing vapors into the air, a number of methods has been employed. For example, aerosol containers have been used to eject vapors into the air upon the activation of a trigger by the user. Other methods, however, utilize the evaporative properties of liquids, or other vaporizable materials, to cause vapors with desired properties to be distributed into the ambient air. One such evaporative method utilizes a wick to deliver a vaporizable liquid from a reservoir to a surface exposed to the ambient air. As the liquid reaches the exposed surface, the liquid is vaporized and dispersed into the ambient air. The exposed surface may be either the surface of the wick or the surface of another body in fluid communication with the wick.

An example of a wick-based, controlled release device is disclosed in U.S. Pat. No. 2,277,377. This patent discloses a device that comprises a cotton wick surrounded by a sheath made of bentonite, a clay-like substance. The device is inserted into a reservoir to lift liquid from the reservoir to the surface of the bentonite sheath. Another method for transporting a liquid to a surface is described in U.S. Pat. No. 4,913,350. This patent discloses an air-freshening device that uses an external, non-porous capillary member to transport the liquid from a reservoir to a surface exposed to the ambient air.

Difficulties can arise, however, when the liquid that is to be transported consists of a mixture of water-based liquids and oil-based liquids. In particular, the oil-based liquids are usually embedded in the water-based liquids and, therefore, the oil-based liquids do not easily reach the exposed surface. Therefore, there is a need for an improved method for transporting water-based and oil-based liquids from a reservoir to a surface.

Although not in the field of fragrance or insecticide release, several techniques have been used to separate oil-based and water-based liquids from one another. For example, U.S. Pat. No. 5,006,264 relates to a method for siphoning water and oil from a mixture of the two. Also, British Patent Specification No. 628,464 discloses that hydrophobic and hydrophilic porous members can be used to separate a mixture of oil-based liquids and water-based liquids. Both of these patents disclose methods of separating oil and water. However, they do not disclose transporting two different types of liquids (i.e., water-based and oil-based) to a surface so that they are in close proximity to one another.

SUMMARY OF THE INVENTION

In one aspect, the present invention provides a composite wick for delivering two liquids with different properties to a surface. The wick comprises a first section provided for delivering a first liquid to the surface of the wick and a second section provided for delivering a second liquid to the surface of the wick.

In another aspect, the present invention provides a device comprising a container for holding a mixture that contains oil-based and water-based liquids, and a porous wick. The porous wick has a first section comprising hydrophobic material and a second section comprising hydrophilic material. The porous wick is positioned so that a lower region of the porous wick will be in contact with the mixture and an upper region of the porous wick is exposed to the ambient air. The first section and the second section will be in contact with the mixture and the ambient air.

In another aspect, the present invention provides a device comprising a container for holding a mixture that contains both oil-based and water-based liquids, and a porous wick that has a first section comprising hydrophobic material and a second section comprising hydrophilic material. The container has an opening at its top surface and the porous wick is positioned in the opening of the container such that a lower region of the porous wick will be in contact with the mixture and an upper region of the porous wick is exposed to the ambient air. The opening in the container is substantially sealed by the porous wick.

In another aspect, the present invention provides a device comprising a container for holding a mixture that contains both oil-based and water-based liquids, and a capillary member that has a first section comprising hydrophobic material and a second section comprising hydrophilic material. The capillary member is positioned such that a lower region of the capillary member will be in contact with the mixture and an upper region of the capillary member is exposed to the ambient air. The first section and the second section will be in contact with the mixture and the ambient air.

In another aspect, the present invention provides a device that comprises a container for holding an oil-based liquid and a water-based liquid, and a porous wick that has a first section comprising hydrophobic material and a second section comprising hydrophilic material. The container has separate compartments for holding each liquid. Also, the porous wick is positioned so that a lower region of the first section will be in contact with the oil-based liquid and a lower region of the second section will be in contact with the water-based liquid, and an upper region of both the first and the second sections is exposed to the ambient air.

In a further aspect, the present invention provides a device comprising a mixture that contains oil-based and water-based liquids, a container for holding the mixture, and a porous wick. The porous wick has a first section comprising hydrophobic material and a second section comprising hydrophilic material. The porous wick is positioned so that a lower region of the porous wick is in contact with the mixture and an upper region of the porous wick is exposed to the ambient air. The first section and the second section are in contact with the mixture and the ambient air.

In another aspect, the present invention provides a device comprising a mixture that contains both oil-based and water-based liquids, a container for holding the mixture, and a porous wick that has a first section comprising hydrophobic material and a second section comprising hydrophilic material. The container has an opening at its top surface and the porous wick is positioned in the opening of the container such that a lower region of the porous wick is in contact with the mixture and an upper region of the porous wick is exposed to the ambient air. The opening in the container is substantially sealed by the porous wick.

In yet another aspect, the present invention provides a device comprising a mixture that contains both oil-based and water-based liquids, a container for holding the mixture, and a capillary member that has a first section comprising hydrophobic material and a second section comprising hydrophilic material. The capillary member is positioned such that a lower region of the capillary member is in contact with the mixture and an upper region of the capillary member is exposed to the ambient air. The first section and the second section are in contact with the mixture and the ambient air.

In still another aspect, the present invention provides a device that comprises an oil-based liquid and a water-based liquid, a container for holding both liquids, and a porous wick that has a first section comprising hydrophobic material and a second section comprising hydrophilic material. The container has separate compartments for holding each liquid. Also, the porous wick is positioned so that a lower region of the first section is in contact with the oil-based liquid and a lower region of the second section is in contact with the water-based liquid, and an upper region of both the first and the second sections is exposed to the ambient air.

In a still further aspect, the present invention provides a composite wick for transporting a liquid to a surface. The wick includes a first section made of either a porous ceramic-based material or a porous sand-based material and a second section made of a porous plastic material. Preferably, the first and second sections are formed as concentric cylinders, with the first section being disposed within the second section.

In yet another aspect, the present invention provides a device that comprises a container for holding a liquid, the container having an opening therein, and a porous wick, having a first section made of either a ceramic-based material or a sand-based material and a second section made of a plastic material. The opening in the container is substantially sealed by the porous wick.

A better understanding of these and other features and advantages of the invention may be had by reference to the drawings and to the accompanying description, in which preferred embodiments of the invention are illustrated and described.

BRIEF DESCRIPTION OF THE DRAWINGS

Throughout the figures, like or corresponding reference numerals have been used for like or corresponding parts.

DESCRIPTION OF THE PREFERRED EMBODIMENTS

A first preferred embodiment of the present invention relates to a system for transporting a mixture of oil-based liquids and water-based liquids from a reservoir to a surface that is exposed to the ambient air. In its simplest form, the device of this invention comprises a container for holding oil-based and water-based liquids, and a two-section wick for transporting the oil-based material and the water-based material from the container to an upper surface of the wick.

Figure 1:
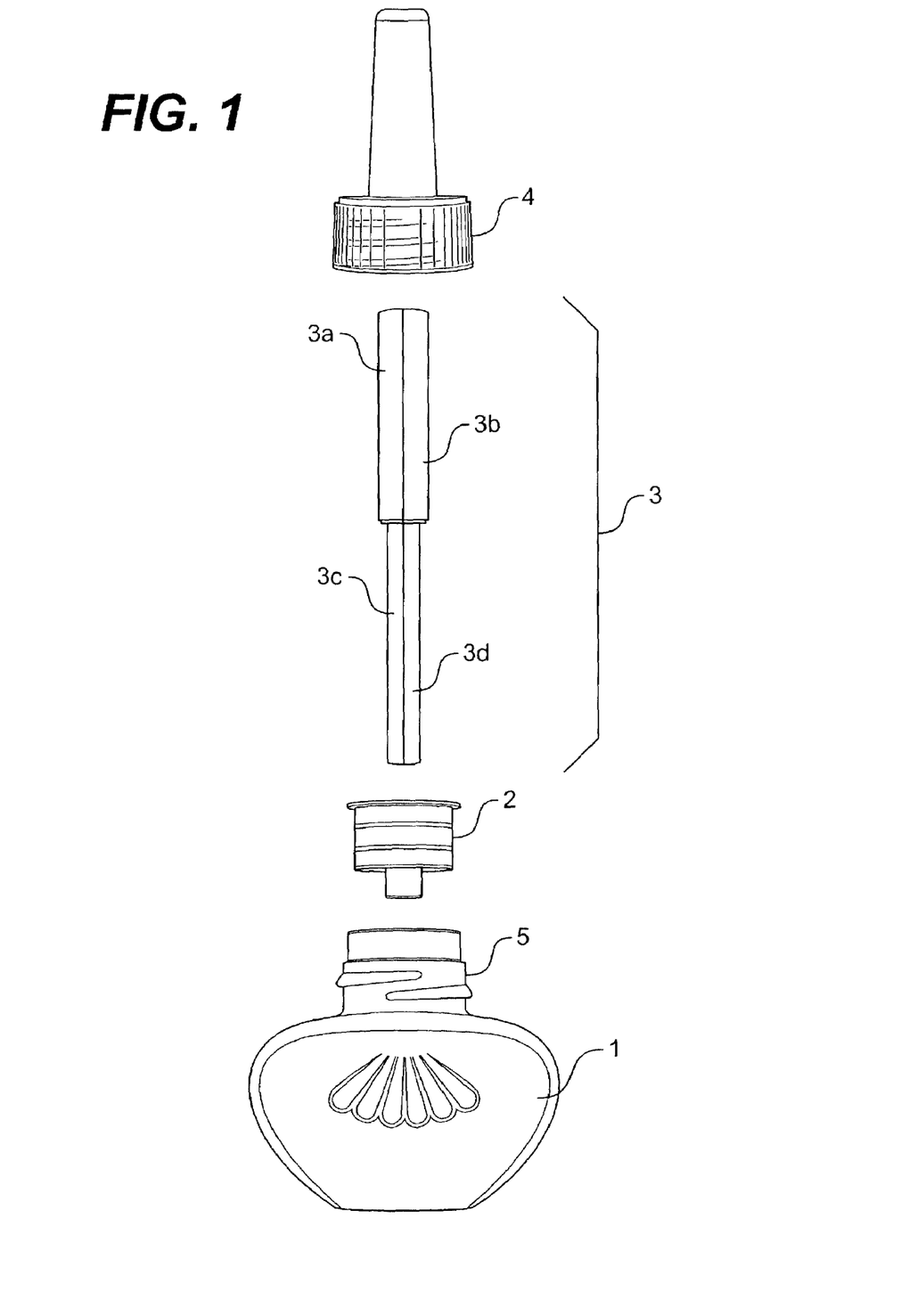
FIG. 1 shows an exploded view of a wick-based delivery system according to a first preferred embodiment of the present invention.

The container can be formed in a variety of shapes. In FIG. 1, for example, the container is a bottle 1 of conventional shape. A wick 3 is shaped so that it fits snugly into the neck 5 of the bottle 1. The wick 3 is long enough so that its bottom surfaces come into contact with the liquid in the bottle 1 and its top surface is exposed to the ambient air. (The level of the liquid is not shown in the bottle 1.) It is preferable to use a neck closure 2, such as that shown in FIG. 1, to hold the wick 3 in place and to prevent leakage around the neck 5 of the bottle 1. The fit between the neck closure 2 and the bottle 1 should be tight enough to prevent leakage of the liquid from the bottle 1. Likewise, the fit between the neck closure 2 and the wick 3 should be sufficiently tight to prevent leakage of the liquid from the bottle 1.

The neck closure 2 or neck 5 of the bottle 1 may be formed with a small hole (e.g., a vent-hole) to help counter the effects of a vacuum that can form in the head-space of the bottle 1. The wick 3 transports the liquid to the surface of the wick 3 by a principle called capillary action. In particular, the wick material contains numerous pores, and these pores act as capillaries, which cause the liquid to be drawn into them. As the liquid is drawn from the bottle 1 and transported up the porous wick 3, a vacuum is created in the head-space of the bottle 1. The formation of a vacuum in the head-space of the bottle 1 decreases the rate that the liquid is wicked from the bottle 1 to the surface. Of course, this decrease in the wicking rate translates directly into a decrease in the release rate of the liquid to the ambient air. Accordingly, in order to combat the formation of the vacuum in the head-space, it is often preferable to form a vent-hole in the vicinity of the head-space of the bottle 1.

In addition, the neck 5 of the bottle 1 can be shaped so that a cover 4 can be securely fastened over the wick 3 and neck closure 2. For example, the outer neck 5 of the bottle 1 may be threaded so that a cover 4 can be screwed on top of the bottle 1 when the device is not in use.

A mixture of oil-based liquids and water-based liquids is added to the bottle 1 in liquid form. The mixture added to the bottle 1 can comprise any variety of materials. If the purpose of the device is to deodorize the air, for example, the mixture can be a liquid combination of fragrances and other liquids which act as the medium for carrying the fragrances.

The present invention is also preferable for use as an insect control product. Insecticides kill insects upon contact with the insecticide or upon ingestion of the insecticide by the insect. Because insecticides work upon physical contact, the insects must be attracted to the insecticide in order for the use of the insecticide to be effective. This is generally accomplished by using a bait or attractant. Since insects need water for their survival, water-based liquids are often used for this purpose. However, it has been found that it is preferable to transport the insecticide in oil-based liquids. Accordingly, we have found that it is preferable to combine water-based liquids (serving as the bait) and oil-based liquids (carrying the insecticide) for use in the present invention.

The bottle 1 and the neck closure 2 can be made of any suitable material that is leakproof. Of course, the size of the opening in the bottle 1 and the size of the neck closure 2 are dependent upon each other and upon the size of the wick 3 that is to be used with the device.

The wick 3 can be made of a variety of materials, depending on the application. We prefer that the wick 3 be rigid enough to provide minimal contact area with the surface that the wick 3 comes in contact with. In the preferred embodiment shown in FIGS. 1 and 2A, the wick 3 comprises two sections made of different materials: hydrophobic sections 3a, 3c and hydrophilic sections 3b, 3d. In FIG. 1, sections 3a, 3c and sections 3b, 3d are separately identified. However, section 3c is the same material as section 3a. Likewise, section 3d is the same material as 3b. Therefore, the hydrophobic sections 3a, 3c can be considered one section, and the hydrophilic sections 3b, 3d can be considered another section. These sections are separately identified in FIG. 1 because the cylindrical shape of the wick 3 is narrowed at its lower region (i.e., sections 3c and 3d) in this example. This narrowing of the wick 3 is not required. The narrowing of the wick 3 is preferred, however, because it increases the surface area of the wick 3 that is exposed to the ambient air and aids in forming a tighter seal at the neck 5 area of the bottle 1.

In FIG. 1, hydrophobic sections 3a, 3c and hydrophilic sections 3b, 3d extend the length of the wick 3. Although it is not necessary that each section extend the full length of the wick 3, each section should be in contact with the liquid in the bottle 1 and the ambient air, in use.

Figure 2A:
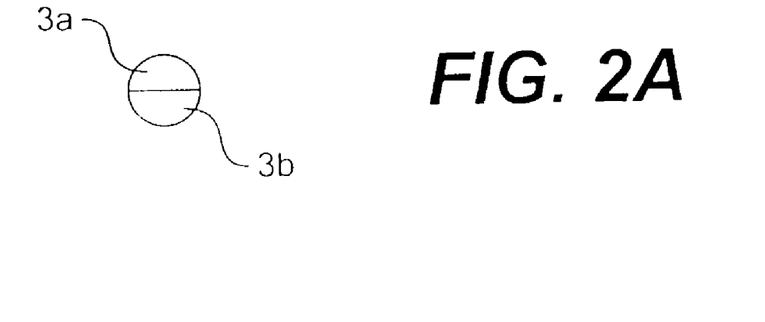
FIG. 2A shows a top view of the wick shown in FIG. 1.

The hydrophobic sections 3a, 3c of the wick 3 can be made of any material that is generally impermeable to water-based liquids. Polymeric wicks, for example, have been found to be effective for these purposes. In particular, wicks composed of ultra high molecular weight high density polyethylene (HDPE) are preferable. Such wicks 3 are generally comprised of blends of HDPE in particle form, and the blends are developed to meet the target pore characteristics of the wick 3.

Preferably, the solubility parameter of the polymer is significantly different from that of any of the components contained in the liquid. This prevents the wick 3 from swelling or other changes that may lead to a change in the pore size and porosity of the wick 3, which would consequentially affect the release rate of the vaporizable liquid into the ambient air.

On the other hand, the hydrophilic sections 3b, 3d of the wick 3 can be made of any material that is generally impermeable to oil-based liquids. Ceramic-based materials, for example, have been found to be effective. Porous ceramic wicks are generally comprised of clay (non-porous) and organic materials (porous). Since the organic materials create the pores in the wick 3, the two types of materials are blended together in a proportion that is appropriate to produce the desired final pore characteristics.

Figure 2B:
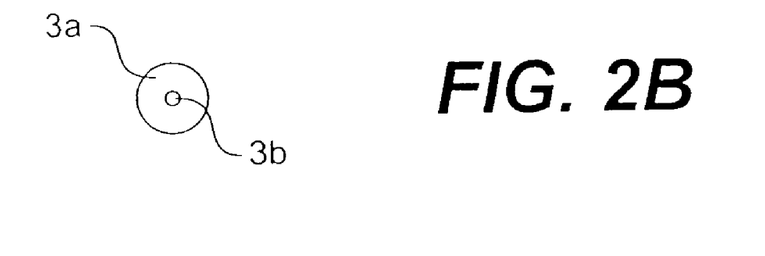
FIG. 2B shows a top view of a wick according to another preferred embodiment of the present invention.

Although FIGS. 1 and 2A depict the hydrophobic and hydrophilic sections of the wick 3 as being side-by-side in the shape of adjoining half cylinders, the two types of sections can be formed in a variety of shapes. The only requirement is that both the hydrophobic section and the hydrophilic section must be in contact with the liquid in the bottle 1 and the ambient air, in use. For example, the two sections could be in the shape of concentric cylinders, as shown in FIG. 2B. It is also not necessary that the hydrophobic section 3a be on the outside of the hydrophilic section 3b as shown in FIG. 2B. In addition, there need not be only two sections of the wick 3. In fact, it may be preferable to have a number of different sections. For example, it may be preferable to have a number of concentric cylinders, with alternating sections of hydrophobic and hydrophilic wick materials.

In addition, it is not necessary that the liquid be in the form of a mixture. Alternatively, the interior of the bottle 1 can consist of multiple compartments that store the oil-based liquids and water-based liquids separately. It is possible, for example, to place the oil-based liquid into one compartment and the water-based material into a second compartment. If the system is designed in this manner, then the wick 3 would have to be altered accordingly.

Figure 3:
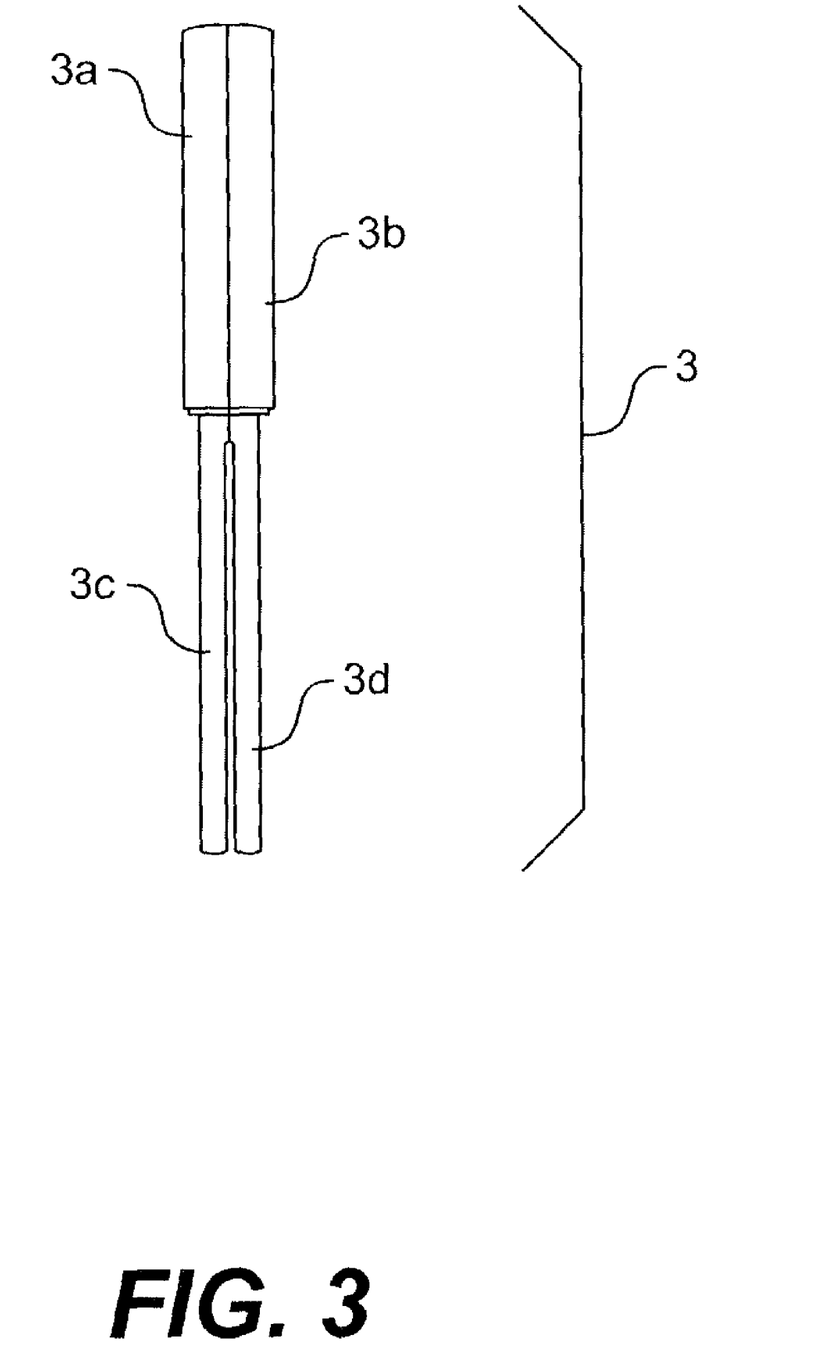
FIG. 3 shows a side view of a wick according to still another preferred embodiment of the present invention.

As shown in FIG. 3, a wick 3 could be used with a bottle 1 that has multiple compartments. For example, the lower region of the wick 3 section that is made of hydrophobic material 3c would extend into the compartment of the bottle 1 that contains the oil-based liquid, and the lower region of the wick section that is made of hydrophilic material 3d would extend into the compartment of the bottle 1 that contains the water-based liquid.

Figure 2C:
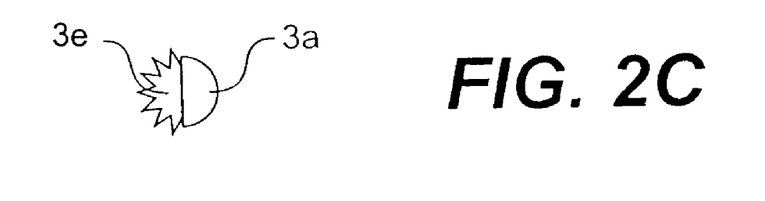
FIG. 2C shows a top view of a wick according to yet another preferred embodiment of the present invention.
Figure 2D:
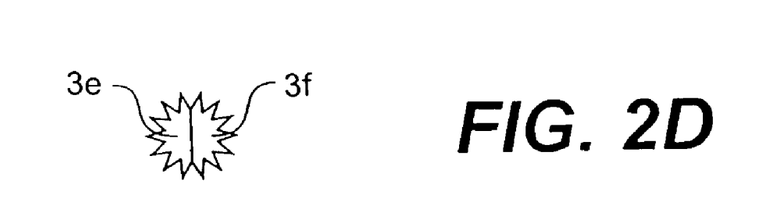
FIG. 2D shows a top view of a wick according to still another preferred embodiment of the present invention.

It is also not necessary that each section of the wick 3 be made up of porous materials. Transport of a liquid from a reservoir to the surface can also be accomplished by using a non-porous, capillary member. Any number of arrangements is envisioned. For example, the wick can be made of a combination of a porous, hydrophobic material (to transport the oil-based material) and a non-porous, hydrophilic material (to transport the water-based material). FIG. 2C shows an embodiment where the hydrophobic section 3a is a porous member and the hydrophilic section 3e is a non-porous capillary member. It is also possible to use two non-porous capillary members as shown in FIG. 2D. In FIG. 2D, the hydrophobic section 3f is a non-porous capillary member and the hydrophilic section 3e is a non-porous capillary member.

The preferred pore size of the porous materials will vary depending upon the composition of the liquid that is to be transported from the reservoir. The term pore size is used to mean the size of the interstices of the material. The mean pore size of a wick 3 can be determined by any standard test for determining porosity and pore size distribution. For example, mercury porosimetry is a method that gives information on porosity and pore size distribution for rigid wicks 3. It is based on the measurement of differential increments in the amount of mercury intruded into the wick 3 as a function of increasing applied pressure.

In the case of insect control, it is generally not desired to have the liquid (either oil-based or water-based) evaporate from the surface of the device. This is because the insects are killed upon contact with the insecticide itself, and not upon contact with a vapor form of the insecticide. Of course, some amount of evaporation will occur and cannot be avoided.

Figure 4:
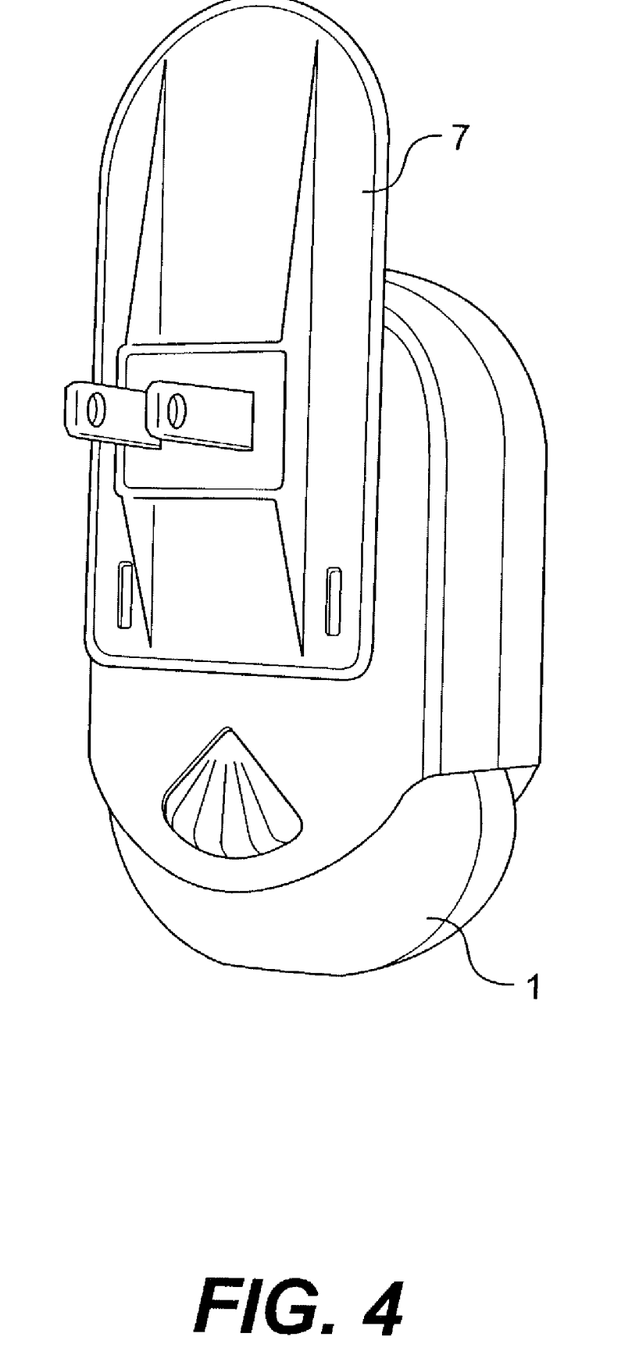
FIG. 4 shows a view of a wick-based delivery system according to the present invention being utilized in conjunction with an optional electric plug-in heater.

In other applications, however, evaporation of the liquid from the surface of the device is preferred. For example, if the liquid in the device is an insect repellant or a deodorizer, it is preferable that the liquid evaporate from the surface of the device into the ambient air. If evaporation is to be encouraged, then our delivery system can be combined with an electric heater to facilitate the release of the vaporizable material into the ambient air. FIG. 4 shows an example of the type of electric heater 7 that may be used for this purpose. In addition, U.S. Pat. No. 5,647,053 describes such an electric plug-in heater and is incorporated herein by reference.

Other means for facilitating the use of the wick-based delivery system of the present invention are also envisioned. For example, the present invention may also be combined with a battery powered fan. Although not required, it is preferable that the wick-based delivery system of this invention be combined with the electric plug-in heater or fan in a removable manner. For example, the wick-based delivery system of the invention may constructed so that the bottle 1 can be combined with an electric plug-in heater 7, for example, in a snap-and-fit manner as shown in FIG. 4.

Figure 5A:
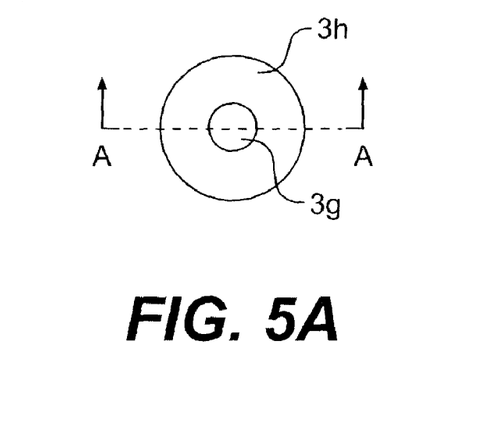
FIG. 5A shows a top view of a wick according to yet another preferred embodiment of the present invention.
Figure 5B:
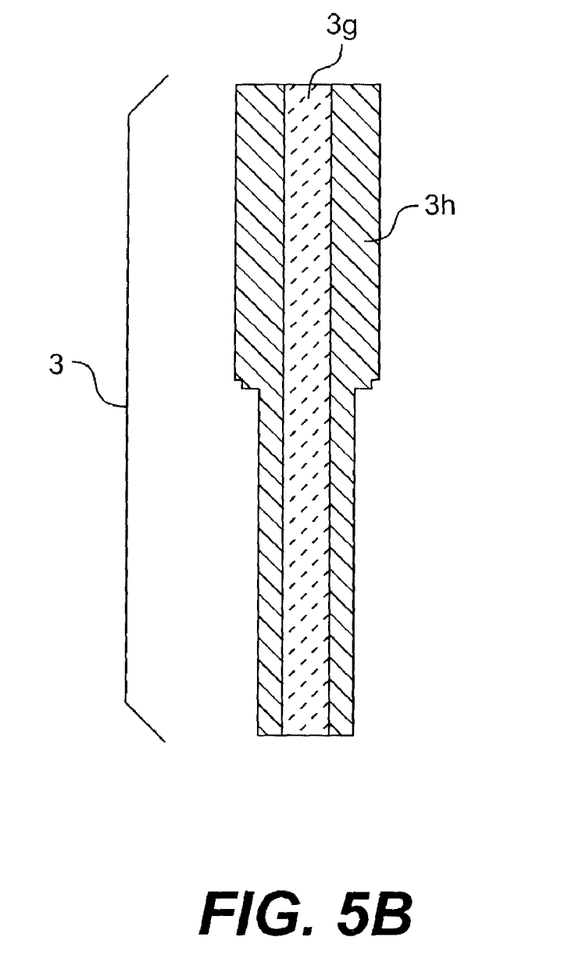
FIG. 5B is a cross-sectional view taken along section line A—A in FIG. 5A.

A wick 3 according to another preferred embodiment of the invention is illustrated in FIGS. 5A and 5B. In this embodiment, the wick 3 comprises two sections 3g and 3h in the shape of concentric cylinders. Preferably, the inner cylinder 3g is comprised of either a porous ceramic-based material or a porous sand-based material, and the outer cylinder 3h is comprised of a porous plastic material. The material of the inner cylinder 3g is selected to provide desirable wicking properties, such as reduced leakage in the case of ceramics, for example. The plastic outer cylinder 3h, meanwhile, protects the inner cylinder 3g from being damaged during manufacturing, distribution, and handling processes. Additionally, the plastic outer cylinder 3h is capable of forming a tighter seal with the neck closure 2 of the bottle 1 (such as shown in FIG. 1) than a strictly ceramic or sand-based wick could form. Those skilled in the art will appreciate that such a composite wick is useful for transporting even a single liquid.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

INDUSTRIAL APPLICABILITY

The present invention provides a device useful as a means to transport liquid to the surface of a device or to disperse vaporized materials into the ambient air. We envision that this device preferably can be used to transport insecticides to an exposed surface or to dispense fragrances, insecticides, and any vaporizable materials into the ambient air to freshen or deodorize the air or to exterminate airborne pests.

We claim:

1. A wick-based delivery system, comprising:
   a container for holding a mixture of oil-based and water-based liquids; and
   a porous wick, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, through the first section, to a surface of the first section that is exposed to the ambient air, and the water-based liquid is transported from within the container, through the second section, to a surface of the second section that is exposed to the ambient air.

2. The wick-based delivery system of claim 1, wherein the first section is comprised of high density polyethylene and the second section is comprised of a ceramic-based material.

3. The wick-based delivery system of claim 1, wherein the wick comprises a plurality of at least one of the first section and the second section.

4. The wick-based delivery system of claim 1, further comprising a heater arranged adjacent to the wick for heating liquid drawn through the wick.

5. The wick-based delivery system of claim 4, wherein the heater is an electric plug-in heater.

6. The wick-based delivery system of claim 1, wherein the container includes an opening that is substantially sealed by the wick.

7. The wick-based delivery system of claim 6, further comprising a neck closure having a hole, wherein the neck closure fits tightly into the opening of the container and the wick fits tightly into the hole of the neck closure, such that the opening of the container is substantially sealed by the neck closure and the wick.

8. A wick-based delivery system, comprising:
   a container for holding a mixture of oil-based and water-based liquids; and
   a capillary member, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, along the first section, to a surface of the first section that is exposed to the ambient air, and the water-based liquid is transported from within the container, along the second section, to a surface of the second section that is exposed to the ambient air.

9. The wick-based delivery system of claim 8, wherein at least one of the first section and the second section is comprised of a non-porous material.

10. The wick-based delivery system of claim 8, wherein one of the first section and the second section is comprised of a porous material, and the other section is comprised of a non-porous material.

11. The wick-based delivery system of claim 8, wherein the first section is comprised of high density polyethylene and the second section is comprised of a ceramic-based material.

12. The wick-based delivery system of claim 8, further comprising a plurality of at least one of the first section and the second section.

13. A wick-based delivery system, comprising:
   a container for holding both an oil-based liquid and a water-based liquid, wherein the container has separate compartments for separately holding the respective liquids; and
   a porous wick, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, through the first section, to a surface of the first section that is exposed to the ambient air, and the water-based liquid is transported from within the container, through the second section, to a surface of the second section that is exposed to the ambient air.

14. The wick-based delivery system of claim 13, wherein the first section is comprised of high density polyethylene and the second section is comprised of a ceramic-based material.

15. The wick-based delivery system of claim 13, wherein the wick comprises a plurality of at least one of the first section and the second section.

16. The wick-based delivery system of claim 13, further comprising a heater arranged adjacent to the wick for heating liquid drawn through the wick.

17. The wick-based delivery system of claim 16, wherein the heater is an electric plug-in heater.

18. The wick-based delivery system of claim 13, wherein the container includes an opening that is substantially sealed by the wick.

19. The wick-based delivery system of claim 18, further comprising a neck closure having a hole, wherein the neck closure fits tightly into the opening of the container and the wick fits tightly into the hole of the neck closure, such that the opening of the container is substantially sealed by the neck closure and the wick.

20. A wick-based delivery system, comprising:
a container for holding an oil-based liquid and a water-based liquid, wherein the container has separate compartments for separately holding the respective liquids; and
a capillary member, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, along the first section, to a surface of the first section that is exposed to the ambient air, and the water-based liquid is transported from within the container, along the second section, to a surface of the second section that is exposed to the ambient air.

21. The wick-based delivery system of claim 20, wherein at least one of the first section and the second section is comprised of a non-porous material.

22. The wick-based delivery system of claim 20, wherein one of the first section and the second section is comprised of a porous material, and the other section is comprised of a non-porous material.

23. The wick-based delivery system of claim 20, wherein the first section is comprised of high density polyethylene and the second section is comprised of a ceramic-based material.

24. The wick-based delivery system of claim 20, further comprising a plurality of at least one of the first section and the second section.

25. A wick-based delivery system, comprising:
a mixture that contains both oil-based and water-based liquids;
a container for holding the mixture; and
a porous wick, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, through the first section, to a surface of the first section that is exposed to the ambient air, and the water-based liquid is transported from within the container, through the second section, to a surface of the second section that is exposed to the ambient air.

26. The wick-based delivery system of claim 25, wherein the first section is comprised of high density polyethylene and the second section is comprised of a ceramic-based material.

27. The wick-based delivery system of claim 25, wherein the wick comprises a plurality of at least one of the first section and the second section.

28. The wick-based delivery system of claim 25, further comprising a heater arranged adjacent to the wick for heating liquid drawn through the wick.

29. The wick-based delivery system of claim 28, wherein the heater is an electric plug-in heater.

30. The wick-based delivery system of claim 25, wherein the container includes an opening that is substantially sealed by the wick.

31. The wick-based delivery system of claim 30, further comprising a neck closure having a hole, wherein the neck closure fits tightly into the opening of the container and the wick fits tightly into the hole of the neck closure, such that the opening of the container is substantially sealed by the neck closure and the wick.

32. A wick-based delivery system, comprising:
a mixture that contains both oil-based and water-based liquids;
a container for holding the mixture; and
a capillary member, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, along the first section, to a surface of the first section that is exposed to the ambient air, and the water-based liquid is transported from within the container, along the second section, to a surface of the second section that is exposed to the ambient air.

33. The wick-based delivery system of claim 32, wherein at least one of the first section and the second section is comprised of a non-porous material.

34. The wick-based delivery system of claim 32, wherein one of the first section and the second section is comprised of a porous material, and the other section is comprised of a non-porous material.

35. The wick-based delivery system of claim 32, wherein the first section is comprised of high density polyethylene and the second section is comprised of a ceramic-based material.

36. The wick-based delivery system of claim 32, further comprising a plurality of at least one of the first section and the second section.

37. A wick-based delivery system, comprising:
an oil-based liquid;
a water-based liquid;
a container for holding both liquids, wherein the container has separate compartments for separately holding the respective liquids; and
a porous wick, having discrete first and second sections, the first section comprising a hydrophobic material and being generally impermeable to the water-based liquid, and the second section comprising a hydrophilic material and being generally impermeable to the oil-based liquid, wherein the oil-based liquid is transported from within the container, through the first section, to a surface of the first section that is exposed to the ambient air, and the water-based liquid is transported from within the container, through the second section, to a surface of the second section that is exposed to the ambient air.

38. The wick-based delivery system of claim 37, wherein the first section is comprised of high density polyethylene and the second section is comprised of a ceramic-based material.

39. The wick-based delivery system of claim 37, wherein the wick comprises a plurality of at least one of the first section and the second section.

40. The wick-based delivery system of claim 37, further comprising a heater arranged adjacent to the wick for heating liquid drawn through the wick.

41. The wick-based delivery system of claim 40, wherein the heater is an electric plug-in heater.

42. The wick-based delivery system of claim 37, wherein the container includes an opening that is substantially sealed by the wick.

43. The wick-based delivery system of claim 42, further comprising a neck closure having a hole, wherein the neck closure fits tightly into the opening of the container and the wick fits tightly into the hole of the neck closure, such that the opening of the container is substantially sealed by the neck closure and the wick.

44. A wick-based delivery system, comprising:
an oil-based liquid;
a water-based liquid;
a container for holding the oil-based liquid and the water-based liquid, wherein the container has separate compartments for separately holding the respective liquids; and
a capillary member, having discrete first and second sections, the first section comprising a hydrophobic material and being generally impermeable to the water-based liquid, and the second section comprising a hydrophilic material and being generally-impermeable to the oil-based liquid, wherein the oil-based liquid is transported from within the container, along the first section, to a surface of the first section that is exposed to the ambient air, and the water-based liquid is transported from within the container, along the second section, to a surface of the second section that is exposed to the ambient air.

45. The wick-based delivery system of claim 44, wherein at least one of the first section and the second section is comprised of a non-porous material.

46. The wick-based delivery system of claim 44, wherein one of the first section and the second section is comprised of a porous material, and the other section is comprised of a non-porous material.

47. The wick-based delivery system of claim 44, wherein the first section is comprised of high density polyethylene and the second section is comprised of a ceramic-based material.

48. The wick-based delivery system of claim 44, further comprising a plurality of at least one of the first section and the second section.

49. A wick-based delivery system, comprising:
a container for holding a mixture that contains both oil-based and water-based liquids; and
a wick, having discrete first and second sections, the first section comprising either a porous, hydrophobic material or a non-porous, hydrophobic capillary member and being generally impermeable to the water-based liquid, and the second section comprising either a porous, hydrophilic material or a non-porous, hydrophilic capillary member and being generally impermeable to the oil-based liquid, wherein the oil-based liquid is transported from within the container, through or along the first section, to a surface of the first section that is exposed to the ambient air, and the water-based liquid is transported from within the container, through or along the second section, to a surface of the second section that is exposed to the ambient air.

50. The wick-based delivery system of claim 49, wherein the first section is comprised of high density polyethylene and the second section is comprised of a ceramic-based material.

51. The wick-based delivery system of claim 49, wherein the wick comprises a plurality of at least one of the first section and the second section.

52. The wick-based delivery system of claim 49, wherein the first and second sections both comprise either a porous material or a non-porous material.

53. A wick-based delivery system, comprising:
a container for holding both an oil-based liquid and a water-based liquid, wherein the container has separate compartments for separately holding the respective liquids; and
a porous wick, having discrete first and second sections, the first section comprising either a porous, hydrophobic material or a non-porous, hydrophobic capillary member and being generally impermeable to the water-based liquid, and the second section comprising either a porous, hydrophilic material or a non-porous, hydrophilic capillary member and being generally impermeable to the oil-based liquid, wherein the oil-based liquid is transported from within the container, through or along the first section, to a surface of the first section that is exposed to the ambient air, and the water-based liquid is transported from within the container, through or along the second section, to a surface of the second section that is exposed to the ambient air and is generally impermeable to the oil-based liquid.

54. The wick-based delivery system of claim 53, wherein the first section is comprised of high density polyethylene and the second section is comprised of a ceramic-based material.

55. The wick-based delivery system of claim 53, wherein the wick comprises a plurality of at least one of the first section and the second section.

56. The wick-based delivery system of claim 53, wherein the first and second sections both comprise either a porous material or a non-porous material.

57. A wick-based delivery system, comprising:
a mixture that contains both oil-based and water-based liquids;
a container for holding the mixture; and
a wick, having discrete first and second sections, the first section comprising either a porous, hydrophobic material or a non-porous, hydrophobic capillary member and being generally impermeable to the water-based liquid, and the second section comprising either a porous, hydrophilic material or a non-porous, hydrophilic capillary member and being generally impermeable to the oil-based liquid, wherein the oil-based liquid is transported from within the container, through or along the first section, to a surface of the first section that is exposed to the ambient air, and the water-based liquid is transported from within the container, through or along the second section, to a surface of the second section that is exposed to the ambient air.

58. The wick-based delivery system of claim 57, wherein the first section is comprised of high density polyethylene and the second section is comprised of a ceramic-based material.

59. The wick-based delivery system of claim 57, wherein the wick comprises a plurality of at least one of the first section and the second section.

60. The wick-based delivery system of claim 57, wherein the first and second sections both comprise either a porous material or a non-porous material.

61. A wick-based delivery system, comprising:
- an oil-based liquid;
- a water-based liquid;
- a container for holding both liquids, wherein the container has separate compartments for separately holding the respective liquids; and
- a porous wick, having discrete first and second sections, the first section comprising either a porous, hydrophobic material or a non-porous, hydrophobic capillary member and being generally impermeable to the water-based liquid, and the second section comprising either a porous, hydrophilic material or a non-porous, hydrophilic capillary member and being generally impermeable to the oil-based liquid, wherein the oil-based liquid is transported from within the container, through or along the first section, to a surface of the first section that is exposed to the ambient air, and the water-based liquid is transported from within the container, through or along the second section, to a surface of the second section that is exposed to the ambient air.

62. The wick-based delivery system of claim 61, wherein the first section is comprised of high density polyethylene and the second section is comprised of a ceramic-based material.

63. The wick-based delivery system of claim 61, wherein the wick comprises a plurality of at least one of the first section and the second section.

64. The wick-based delivery system of claim 61, wherein the first and second sections both comprise either a porous material or a non-porous material.

\* \* \* \* \*